(12) United States Patent
Chung

(10) Patent No.: US 12,426,862 B2
(45) Date of Patent: Sep. 30, 2025

(54) IMPLANT FOR SCREENING TEST OF OVARIAN CANCER, SCREENING TEST KIT COMPRISING SAME, AND OVARIAN CANCER SCREENING TEST METHOD USING SAME

(71) Applicant: MCAREKOREA CO. LTD., Seongnam (KR)

(72) Inventor: Hyun Hoon Chung, Seoul (KR)

(73) Assignee: CHUNGMED USA, INC., Rockville, MD (US)

( * ) Notice: Subject to any disclaimer, the term of this patent is extended or adjusted under 35 U.S.C. 154(b) by 772 days.

(21) Appl. No.: 17/423,436

(22) PCT Filed: Jul. 30, 2019

(86) PCT No.: PCT/KR2019/009483
§ 371 (c)(1),
(2) Date: Jul. 15, 2021

(87) PCT Pub. No.: WO2020/196998
PCT Pub. Date: Oct. 1, 2020

(65) Prior Publication Data
US 2022/0110615 A1  Apr. 14, 2022

(30) Foreign Application Priority Data
Mar. 27, 2019  (KR) .................. 10-2019-0034853

(51) Int. Cl.
*A61B 10/02* (2006.01)
*A61B 10/04* (2006.01)
(Continued)

(52) U.S. Cl.
CPC .......... *A61B 10/0291* (2013.01); *A61B 10/04* (2013.01); *A61F 6/144* (2013.01); *A61F 6/18* (2013.01)

(58) Field of Classification Search
CPC ..... A61B 10/0291; A61B 10/04; A61B 10/02; A61F 6/144; A61F 6/18
See application file for complete search history.

(56) References Cited

U.S. PATENT DOCUMENTS 4,727,866 A * 3/1988 Livesay ................ A61B 5/062
324/251
6,080,129 A * 6/2000 Blaisdell ............ A61M 31/005
128/898
(Continued)

FOREIGN PATENT DOCUMENTS

KR  20150136143 A  12/2015
KR  20160007484 A  1/2016
(Continued)

*Primary Examiner* — Alex M Valvis
*Assistant Examiner* — Jonathan M Haney
(74) *Attorney, Agent, or Firm* — Han's Law Office

(57) ABSTRACT

The present invention relates to an implant, an ovarian cancer screening test kit comprising same, and an ovarian cancer screening test method using same, thereof wherein the implant is mounted in the uterine cavity so that the working channel maintain a path from the cervix to the fallopian tube for a predetermined period. According to the implant for screening test of ovarian cancer, the screening test kit comprising same, and the ovarian cancer screening test method using same of the present invention, the implant mounted in the uterus can be used to execute the screening test, can simply carry out periodically repeated screening tests to improve the convenience and minimize discomfort for the patient, and can allow both cystoscopy and biopsy.

6 Claims, 23 Drawing Sheets

(51) Int. Cl.
*A61F 6/14* (2006.01)
*A61F 6/18* (2006.01)

(56) References Cited

U.S. PATENT DOCUMENTS

| | | | |
|---|---|---|---|
| 7,320,325 | B2 | 1/2008 | Duchon et al. |
| 8,585,616 | B2 * | 11/2013 | Swann ............. A61B 17/12136 |
| | | | 604/93.01 |
| 11,116,675 | B2 * | 9/2021 | Miller .................... A61B 10/04 |
| 2005/0033163 | A1 * | 2/2005 | Duchon .............. A61M 31/002 |
| | | | 600/431 |
| 2007/0151565 | A1 * | 7/2007 | Sanders Acedo ......... A61F 6/18 |
| | | | 128/839 |
| 2010/0216137 | A1 * | 8/2010 | Bankaitis-Davis .. C12Q 1/6886 |
| | | | 435/6.14 |
| 2013/0078319 | A1 * | 3/2013 | Levine ............... A61B 10/0291 |
| | | | 435/7.92 |
| 2016/0278747 | A1 * | 9/2016 | Chin .................. A61B 10/0291 |
| 2017/0119278 | A1 * | 5/2017 | Hyde ...................... A61B 5/11 |
| 2019/0015247 | A1 * | 1/2019 | Wildemeersch ........ A61F 6/144 |

FOREIGN PATENT DOCUMENTS

| | | |
|---|---|---|
| WO | WO9524149 A1 | 9/1995 |
| WO | WO9713451 A1 | 4/1997 |

* cited by examiner

IMPLANT FOR SCREENING TEST OF OVARIAN CANCER, SCREENING TEST KIT COMPRISING SAME, AND OVARIAN CANCER SCREENING TEST METHOD USING SAME

This application is a national stage application, filed under 35 U.S.C. § 371, of International Patent Application No. PCT/KR2019/009483, filed on Jul. 30, 2019, which claims the priority of Korean application No. 10-2019-0034853, filed on Mar. 27, 2019, the contents of which are incorporated by reference.

TECHNICAL FIELD

The present disclosure relates to an implant for screening test of ovarian cancer, a screening test kit including the same, and an ovarian cancer screening test method using the same, and more particularly, to an implant capable of performing an ovarian cancer screening text repeatedly at regular intervals, a screening test kit including the same, and an ovarian cancer screening test method using the same.

BACKGROUND ART

Ovarian cancer accounts for about 20% of gynecological cancers, and in most cases, there are no specific symptoms even in advanced stage. Therefore, it is known that ovarian cancer has the worst prognosis among gynecological cancers because ovarian cancer is often detected as stage 3 or higher at the time of diagnosis. For example, epithelial ovarian cancer, which accounts for about 90% of ovarian cancers, is also found at stage 3 or higher, and the prognosis thereof is so poor that the five-year relative survival rates is reported to be about 40%.

Although the diagnosis of ovarian cancer is made through surgery, if a lesion suspected of ovarian cancer is detected before the surgery, tests are performed to check the progress of the disease and whether the cancer has metastasized to the surrounding organs. Conventionally, ovarian cancer is inferred by performing imaging diagnosis using ultrasound, imaging diagnosis such as computed tomography (CT) or magnetic resonance imaging (MRI), and analysis of serum tumor markers such as CA-125, but there is no way to screen for or diagnose the ovarian cancer in advance. Meanwhile, in relation to the conventional screening for ovarian cancer, U.S. Pat. No. 8,486,648 has been disclosed.

Meanwhile, regarding the ovarian cancer, recent research results have been reported that high-grade serous carcinoma, which accounts for a significant portion of ovarian cancer, begins in the fallopian tubes, not the ovaries. Therefore, there is a need for a screening test method different from the conventional ovarian cancer screening test.

DISCLOSURE

Technical Problem

The present disclosure provides an implant which helps screening and early diagnosis of ovarian cancer, a screening test kit including the same, and an ovarian cancer screening test method using the same, unlike the current clinical practice for finding ovarian abnormalities.

Technical Solution

In an aspect, there may be provided an implant including: a body part extending to a predetermined length so as to be inserted into uterine cavity; an arm extending from the body part and having at least a portion to be inserted into a fallopian tube; and a working channel formed through the arm from an end portion of the body part, and configured to allow an insertion instrument to be inserted therein from an outside, and wherein the implant is mounted in the uterine cavity so that the working channel maintain a path from the cervix to the fallopian tube.

The implant may be inserted into the uterine cavity through a cervix, and at least a portion of the implant may be formed of a soft material so that the implant is mounted in the uterus in a state at least a portion of the arm is inserted into the fallopian tube.

Meanwhile, at least one of the body part and the arm may include a curved portion.

In addition, the implant may further include a protrusion that prevents the arm from coming off from the fallopian tube in a case where the implant is mounted in the uterine cavity.

Meanwhile, the arm may be configured as one pair of arms formed to extend from both sides of the body part in directions away from each other.

In addition, the working channel may be configured as one pair of working channels each formed from the end portion of the body part through each of the pair of arms.

In addition, the working channel may include a tapered portion formed at the end portion of the body part so as to smoothly guide the insertion of the insertion instrument.

Meanwhile, at least one of the body part and the arm may include a hormone releasing part configured to release hormones for a predetermined period while inserted into the uterine cavity.

In another aspect, there may be provided an ovarian cancer screening test kit including: an endoscope capable of being inserted into a fallopian tube; an implant mounted in uterine cavity; and an insertion instrument to enter the fallopian tube from cervix through the implant, and the implant may include: a body part extending to a predetermined length so as to be inserted into the uterine cavity; an arm extending from the body part and having at least a portion to be inserted into the fallopian tube; and a working channel formed through the arm from an end portion of the body part, and configured to allow an insertion instrument to be inserted therein from an outside, and the working channel is mounted in the uterine cavity so as to maintain a path from the cervix to the fallopian tube.

The ovarian cancer screening test kit may be configured so that the implant is mounted in the uterine cavity for a predetermined period including a non-test period.

Meanwhile, the insertion instrument may be configured to capture or extract tissues including epithelial cells in the fallopian tube.

In addition, the insertion instrument may include a micro-robot provided at an end portion of the insertion instrument and configured to capture or extract cells in the fallopian tube.

Further, the micro-robot may include: at least one extension part extending in a radial direction to be in contact with an inner wall of the fallopian tube, and an extraction part provided at a distal end portion of the extension part and configured to capture or extract cells.

In addition, the micro-robot may include an actuator configured to be transformable between a first shape in which the expansion part is contracted so as to pass through the working channel and a second shape in which the expansion part is expanded in the fallopian tube.

In addition, the extraction part may have a curved outer surface, and at least a portion of the outer surface may be allowed to come in surface contact with the inner wall of the fallopian tube.

In yet another aspect, there may be provided an ovarian cancer screening test method including: inserting an insertion instrument into a vaginal canal; entering the insertion instrument into a fallopian tube through a working channel of an implant mounted in advance in uterine cavity; obtaining cells or tissues in the fallopian tube with the insertion instrument; withdrawing the insertion instrument out of a human body; and screening the cells or the tissues.

The implant may include: a body part having at least a portion thereof positioned in the uterine cavity; an arm of which at least a portion of the other end is inserted into the fallopian tube; and a working channel formed through the body part and the arm.

Meanwhile, the implant may be mounted in the uterine cavity by performing operations including: inserting a guide wire or an endoscope into a working channel through an opening of the body part, and withdrawn by a predetermined length through an opening of the arm; inserting a sheath into a cervix; inserting an end portion of the guide wire or the endoscope into the fallopian tube via a channel of the sheath; inserting the implant into the uterine cavity through the channel of the sheath and inserting at least a portion of the arm into the fallopian tube along the endoscope; removing the guide wire or the endoscope; and removing the sheath so that the implant is mounted in the uterine cavity.

Meanwhile, the ovarian cancer screening test method may be performed periodically after the implant is mounted.

Meanwhile, the screening may include screening for high-grade serous intraepithelial carcinoma.

Advantageous Effects

According to the implant for screening test of ovarian cancer, the screening test kit comprising same, and the ovarian cancer screening test method using same of the present invention, the implant mounted in the uterus can be used to perform the screening test, can simply carry out periodically repeated screening tests to improve the convenience and minimize discomfort for the patient, and can allow both cystoscopy and biopsy.

MODE FOR DISCLOSURE

Figure 1:
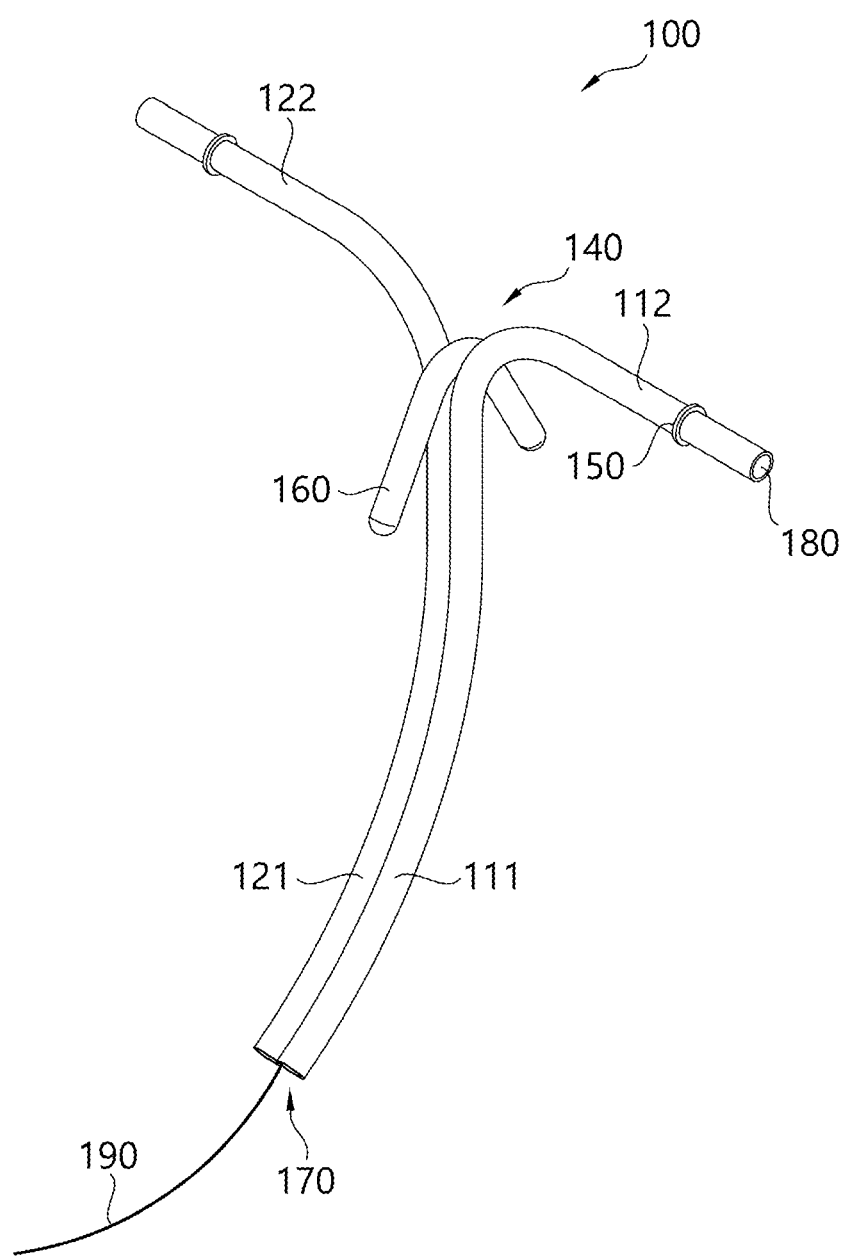
FIG. 1 is a perspective view of an implant which is a first embodiment according to the present disclosure.

Hereinafter, an implant for screening test of ovarian cancer according to an embodiment of the present disclosure, a screening test kit including the same, and an ovarian cancer screening test method using the same will be described in detail with reference to the accompanying drawings. In addition, in a description of the following exemplary embodiment, a name of each constituent element may be referred to as a different name in the art. However, when the constituent elements have functional similarity and identity, even if a changed exemplary embodiment is adapted, the constituent elements may be regarded as equivalent elements. Further, for convenience of a description, a reference numeral is added to each constituent element. However, contents shown on a drawing having these reference numerals do not limit a range of each constituent element to a range within the drawing. Similarly, even if an exemplary embodiment is adapted in which a constituent element on a drawing is partially changed, when the constituent elements have functional similarity and identity, the constituent elements may be regarded as equivalent elements. Further, when the constituent element is recognized as a constituent element that should be naturally included in a level of a person of ordinary skill in the art, a detailed description thereof will be omitted.

Hereinafter, the uterine cavity refers to an anatomically empty space inside the uterus, and the fallopian tube (or fallopian tube) refers to a tube-shaped tissue from the uterus to the ovaries.

In addition, hereinafter, the periodic screening test refers to an examination that can be repeatedly performed at a predetermined time interval, where the predetermined time may be several days to several months, and it will be described on the premise that the predetermined time may vary depending on the condition of a patient. Meanwhile, the implant according to the present disclosure may be inserted and mounted for a woman who has sexual intercourse and does not plan to give birth or a woman who cannot give birth due to menopause.

Hereinafter, an implant according to the present disclosure will be described in detail with reference to FIGS. 1 to 4.

Figure 2A:
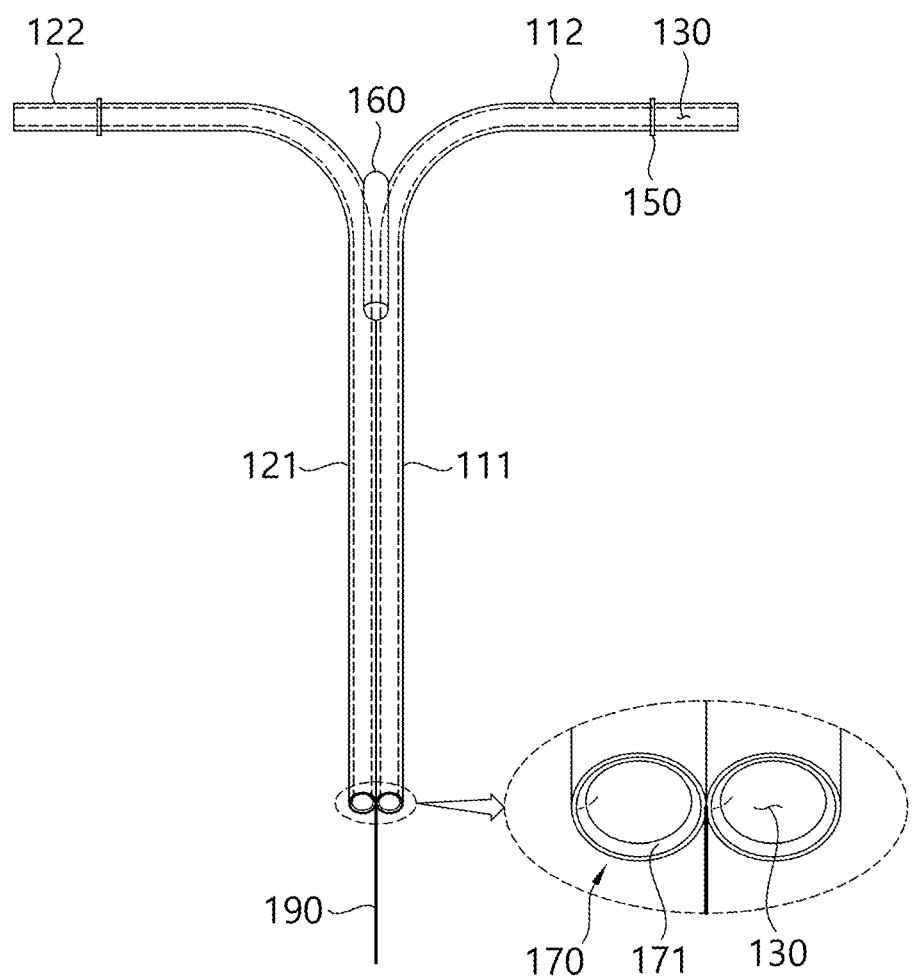
FIGS. 2A and 2B are a plan view, a front view, and a partially enlarged view of the first embodiment.
Figure 2B:
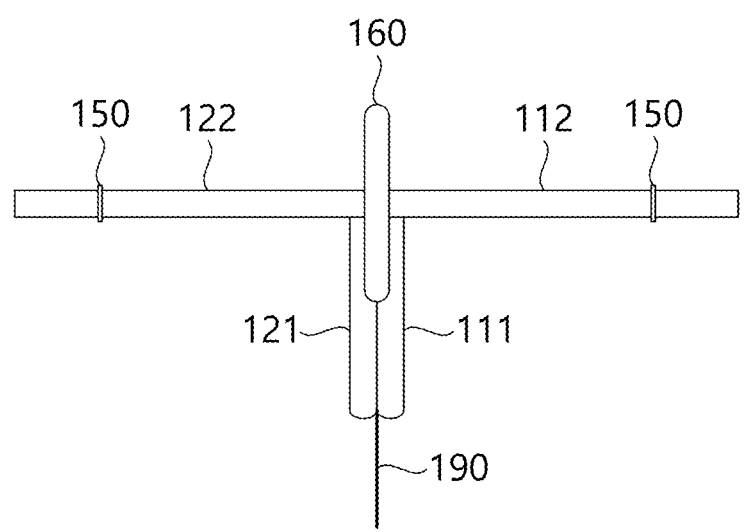

FIG. 1 is a perspective view of an implant which is a first embodiment according to the present disclosure, and FIGS. 2A and 2B are a plan view, a front view, and a partially enlarged view of the first embodiment.

As shown, an implant 100 according to the present disclosure may be configured to be inserted and mounted in uterine cavity 12. When mounted in the uterus 11, the implant 100 may be configured such that a working channel 130 is disposed in a path from cervix 13 to a fallopian tube 14. The implant 100 may include, for example, a body part, an arm, a protrusion 150, a working channel 130, a support part 160, and a fiber 190. Meanwhile, the implant 100 may include a body part, an arm, a protrusion 150 and a working channel 130 as a pair, and may be configured symmetrically.

Looking at the configuration of one side of the implant 100, a first body part 111 and a first arm 112 may be connected to each other. The first body part 111 may be formed to extend in a longitudinal direction, and the first body part 111 may be configured to include a curved portion 140 that is slightly bent forward to correspond to the anatomical shape of the uterine cavity 12 when mounted in the uterine cavity 12. One end of the first body part 111 may have a length that can be positioned in the cervix 13 when the implant 100 is mounted in the uterus 11.

The first arm 112 is provided at the other end of the first body part 111. One side of the first arm 112 may be connected to the first body part 111, and the other side thereof may be formed at a predetermined angle with the body part so that the implant 100 can be inserted into any one of the fallopian tube 14 when the implant 100 is mounted in the uterine cavity 12. The first arm 112 may be configured to include a curved portion 140 bent in the right direction in FIG. 2A. The first arm 112 may be configured with an appropriate outer diameter for insertion into the fallopian tube 14. Statistically, since the fallopian tube 14 has a length of 10 to 13 cm and an inner diameter of 0.5 to 1.2 cm, it is preferable that the first arm 112 has a length of 13 cm or less and an outer diameter of 1.2 cm or less.

The protrusion 150 is configured to maintain the position in which the first arm 112 is inserted into the fallopian tube 14. The protrusion 150 is formed to protrude outward from one side of the first arm 112, and the position of the protrusion 150 may be fixed so as to prevent apart of the mechanically inserted first arm 112 from escaping from the fallopian tube 14. The protrusion 150 may be inserted into the fallopian tube 14 together with a portion of the first arm 112, may be fixed in close contact with the fallopian tube 14 in a radial direction, or may be fixed while expanding the fallopian tube 14 in the radial direction. When the protrusion 150 is positioned in the fallopian tube 14, the protrusion 150 may be fixed while the protrusion 150 is pressed by elasticity of the fallopian tube 14 itself.

The working channel 130 may be configured through the first body part 111 and the first arm 112. The working channel 130 may extend from a first opening 170 formed in an end portion of the first body part 111 and may be formed up to a second opening 180 formed in an end portion of the first arm 112. The working channel 130 is configured so that an endoscope 300 and an insertion instrument 200 to be described later can be inserted. Meanwhile, the first opening 170 may include a tapered portion 171 which is formed with an enlarged inner diameter so that insertion can be made easily. The working channel 130 may be formed to have a smooth surface so that the endoscope 300 or the insertion instrument 200 can be smoothly inserted along a path from the first opening 170 to the second opening 180. However, although not illustrated, a door capable of shielding the first opening 170 may be provided. Since the working channel 130 of the implant 100 may function as a passage through which substances in the vagina can move to the fallopian tube 14 in daily lives where the working channel 130 of the implant 100 is not used, the door is used to block the working channel 130. The door may be configured to be detachable to selectively open and close the working channel 130.

Meanwhile, the above-described first body part 111 and the first arm 112 may be configured to be soft to be appropriately deformed in response to the diversity of anatomical structures. Here, the first arm 112 may be configured to be softer than the body part so that the first arm 112 can be naturally mounted in the path toward the fallopian tube 14 and in the fallopian tube 14. In an example, the first arm 112 may be made of a more flexible material than the first body part 111 and may be attached to each other, and the first arm 112 may be configured such that the first body part 111 is integrally formed and the first arm 112 is configured to have a thinner thickness than that of the first body part 111 to increase ductility. However, it is preferable that the first body part 111 and the first arm 112 are made of a material and a thickness that are sufficient to secure the working channel 130 even when deformation is made.

The above-described first body part 111, the first arm 112, the protrusion 150, and the working channel 130 are configured as a pair and may be configured symmetrically. That is, the first body part 111 and a second body part 121 may be provided to extend in parallel, and the first arm 112 and a second arm 122 may be formed to extend away from each other. Here, since the fallopian tube 14 is present on both left and right sides from the uterus 11, the configuration of the first arm 112 and the second arm 122 may be configured to be inserted into the both fallopian tubes. Meanwhile, since the configuration of the second body part 121 and the second arm 122 may be the same as that of the first body part 111 and the first arm, a detailed description thereof will be omitted.

The support part 160 is configured so that the body part does not come off in the uterus 11. The support part 160 may be formed to extend at a predetermined angle with a body part on one side of the body part. Specifically, the body part may be formed to extend in a downward direction to prevent movement in the downward direction when the implant 100 is inserted. The support part 160 may be formed with a central portion connected to the first body part 111 and the second body part 121 and extending to the front and rear sides, respectively. However, the above-described shape of the support part 160 is merely an example, and the shape of the support unit 160 may be modified and applied in various configurations that allows the implant 100 to be mounted in the uterus 11 and prevents the implant 100 from coming off. Meanwhile, the support part 160 may be formed of a soft material, and the support part 160 may be formed of a soft material so that the support part 160 contracts when entering the uterine cavity 12 through the cervix 13, and expands in the uterine cavity 12 to support the inner wall of the uterus 11. However, as will be described later, it is preferable to select a strength of the support part 160 that allows smooth deformation and extraction while preventing tissue damage when permanently removing the implant 100 outside the human body.

The fiber 190 is configured to transmit a traction force from the outside when the implant 100 is removed. The fiber 190 is configured so that the implant 100 can be discharged from the uterus 11 by pulling the fiber 190 toward the entrance of the vaginal canal 16. The fiber 190 may be configured to be positioned inside the vaginal canal 16 even when the implant 100 is mounted in the uterus 11. For example, the fiber 190 may be configured at one end portion of at least one of the first body part 111 and the second body part 121 to have a predetermined length.

Meanwhile, although not illustrated, it may further include a hormone releasing part (not shown) configured to secrete hormones within the uterus 11 for a predetermined period of time. The hormone releasing part may include, for example, for the purpose of contraception or treatment of endometrial lesions, and so forth and may be provided on one side of the implant 100.

Figure 3:
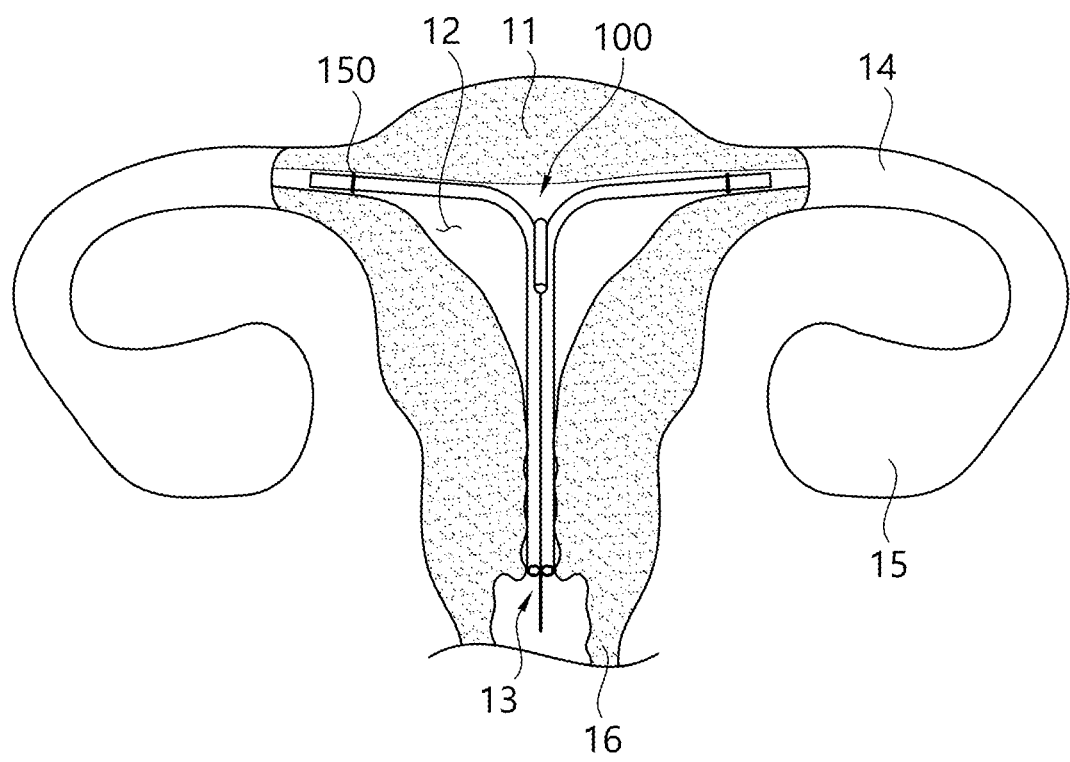
FIG. 3 is a conceptual diagram illustrating a concept in which an implant is mounted in the uterus.
Figure 4:
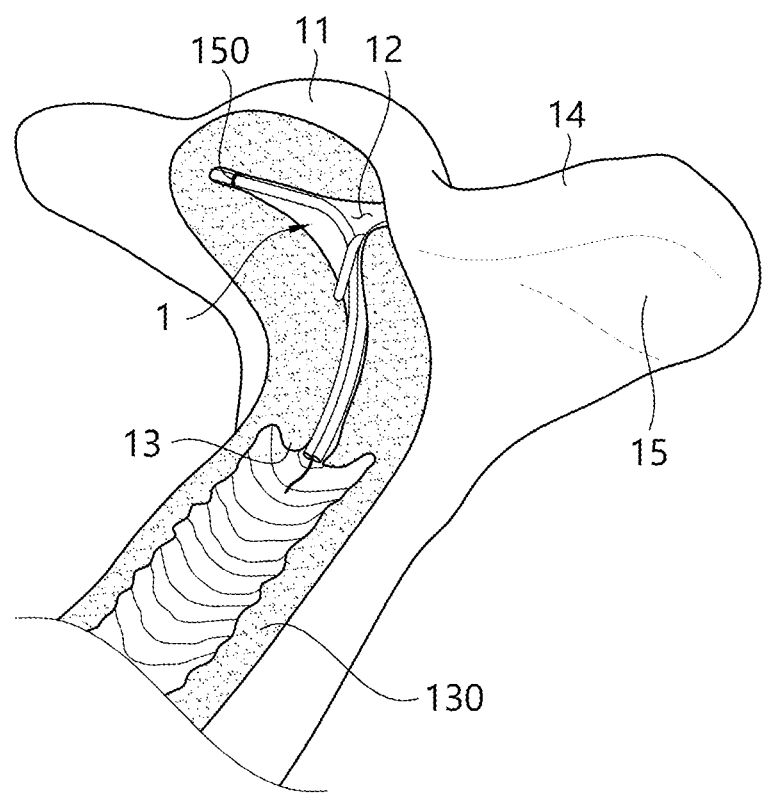
FIG. 4 is a conceptual diagram illustrating FIG. 3 from another angle.

FIG. 3 is a conceptual diagram illustrating a concept in which the implant 100 is mounted in the uterus 11, and FIG. 4 is a conceptual diagram illustrating FIG. 3 from another angle.

As illustrated, when the implant 100 is mounted, the first opening 170 of each of the first body part 111 and the second body part 121 is positioned in the cervix 13, and the first arm 112 and the second arm 122 is configured to be inserted into the fallopian tube 14 on the both sides. The support part 160 may be completely positioned in the uterine cavity 12 and mounted therein. Therefore, even in daily lives with the implant 100 being mounted, a user is not affected by the implant 100 and the implant 100 does not easily come off the uterus 11.

The pair of left and right working channels 130 formed in the implant 100 form a path from the cervix 13 to the left and right fallopian tubes 14 to facilitate the collection or extraction of cells in the fallopian tubes 14. In other words, in a case where extraction of cells or tissues from the fallopian tube 14 is performed periodically, the implant 100 that has already been mounted is used even if the path from the cervix 13 to the fallopian tube 14 is not secured during each screening test, and thus, the screening test may be performed easily.

Hereinafter, a screening test kit including the implant 100 will be described with reference to FIGS. 5, 6, 7A, 7B, 7C and 7D.

Figure 5:
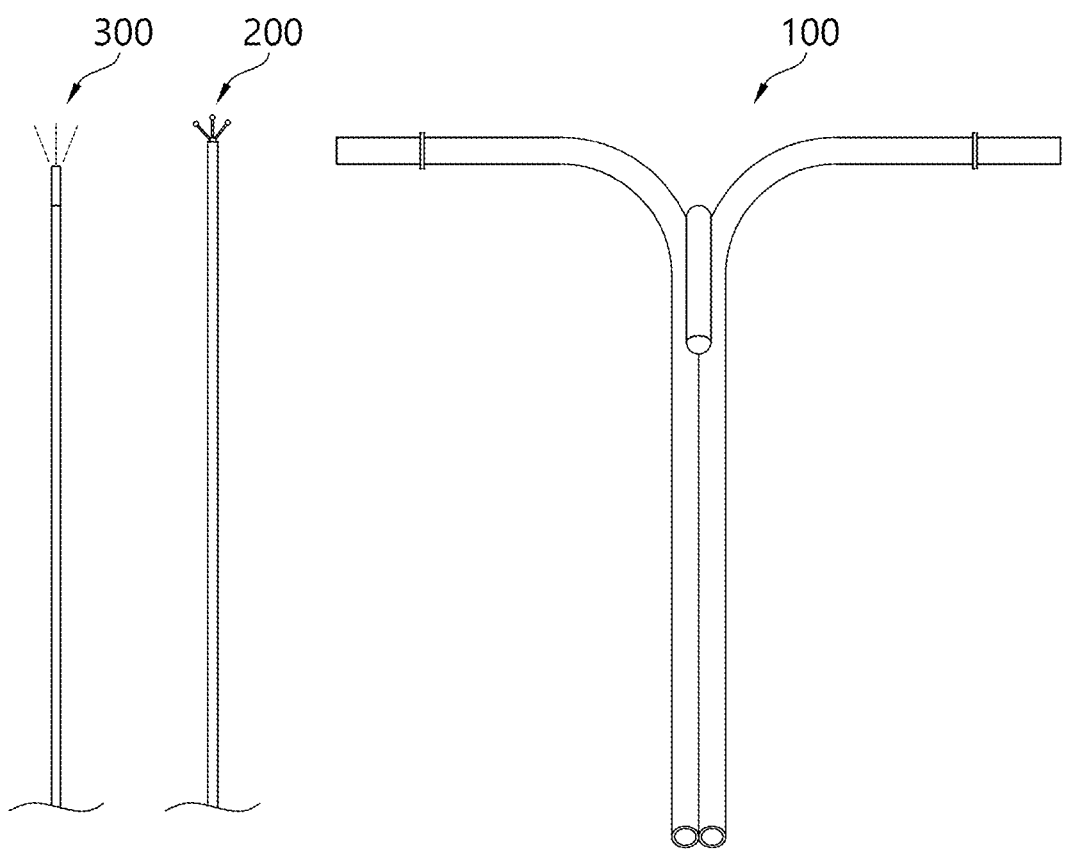
FIG. 5 is a conceptual diagram of a screening test kit including an implant, which is another embodiment according to the present disclosure.
Figure 6:
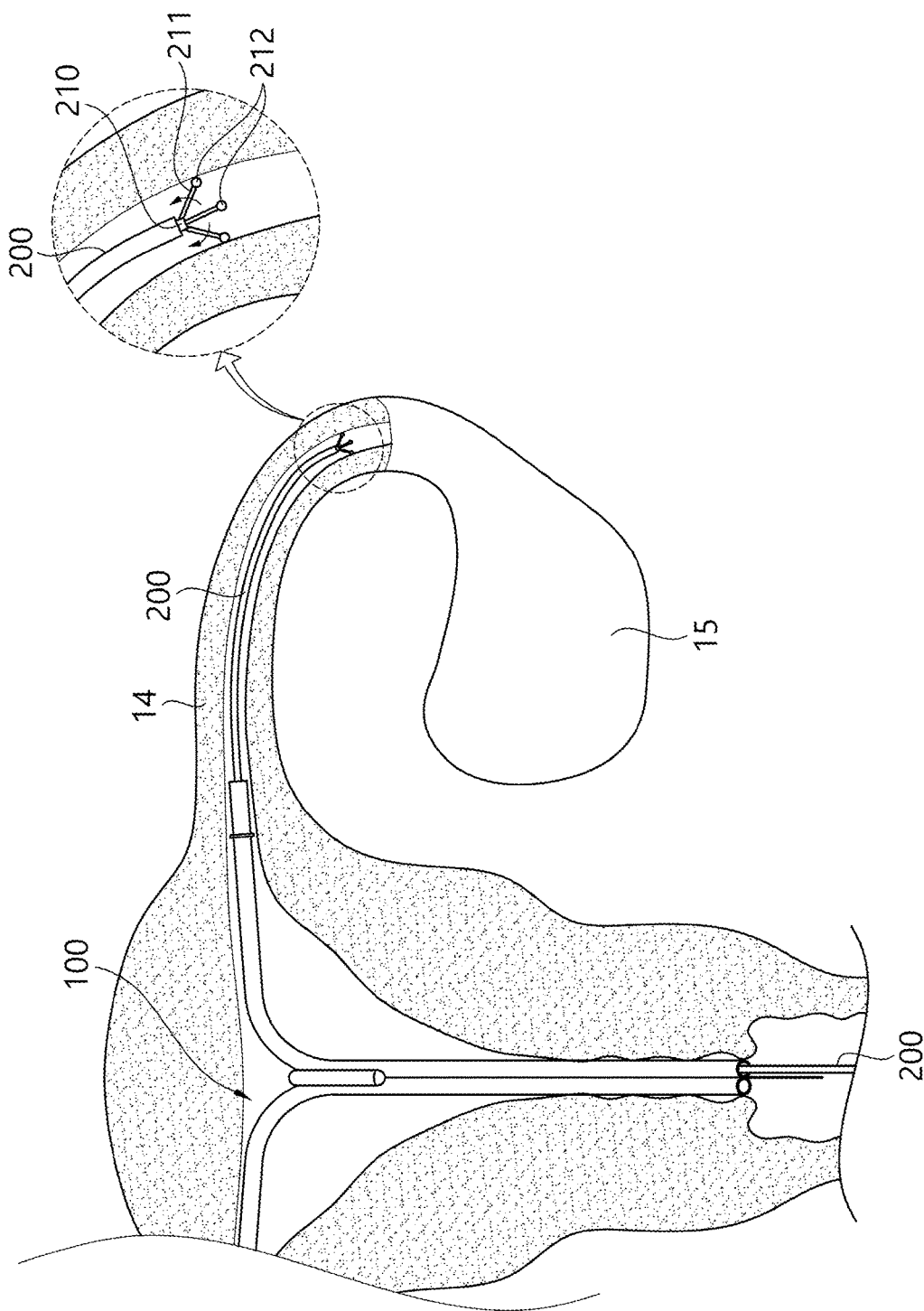
FIG. 6 is a state diagram of a test kit in use.

FIG. 5 is a conceptual diagram of a screening test kit including the implant 100, which is another embodiment according to the present disclosure, and FIG. 6 is a state diagram of the screening test kit.

As illustrated, the screening test kit including the implant 100 may be configured to include the implant 100, the endoscope 300, and the insertion instrument 200. Here, the implant 100 may be configured to be mounted in the uterus 11 as described above. The endoscope 300 and the insertion instrument 200 may be configured to have an outer diameter smaller than an inner diameter of the working channel 130 so that the endoscope 300 and the insertion instrument 200 can be inserted into the working channel 130 of the implant 100 and move smoothly therein.

The endoscope 300 is configured to acquire an image at an end portion thereof. The endoscope 300 may be used as a guide when the implant 100 is installed, and may be configured to acquire visual information during a screening test in the fallopian tube 14. In particular, in the case of acquiring an image of the inside of the fallopian tube 14, the endoscope 300 enters directly into the fallopian tube 14 through the first opening 170 of the implant 100 without going through complicated operations and procedures for insertion into the fallopian tube 14 at each screening test.

The insertion instrument 200 may be configured to obtain cells or tissues from the fallopian tube 14. The insertion instrument 200 may be configured as a tube extending in the longitudinal direction, and may be formed of a soft material so that the insertion instrument 200 can enter into a curved path along the working channel 130 of the implant 100.

A micro-robot 210 that can be retracted from the end of the insertion instrument 200 may be further included. For example, the micro-robot 210 may be positioned inside the tube when in a first shape which is a contracted state, and may be controlled to be transformed to a second shape in an expanded state when exposed to the outside. The micro-robot 210 is configured to include: a plurality of extension parts 211 configured to be radially expanded by driving of an actuator and to be in contact with an inner wall of the fallopian tube 14; and extraction parts 212 respectively provided at end portions of the extension parts 211. As an example, the extension parts 211 may be composed of three extensions and may be disposed along a circumference at intervals of 120 degrees. An outer surface of each extraction part 212 is configured to be in a curved shape so as to come in surface contact with the inner wall of the fallopian tube 14, and is configured to rotate relative to the expansion parts 211. Each extraction part 212 is configured in the form of a sphere, for example, and a plurality of grooves configured in a predetermined pattern may be provided on the outer surface of each extraction part 212 to capture cells. After capturing the cells, the micro-robot 210 may contract into the first shape and move the cells to the inside of the tube, and the cells captured by the tube may be protected and may be taken out along the working channel 130 to the outside.

Figure 7A:
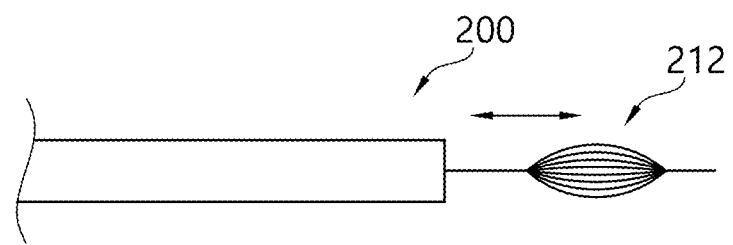
FIGS. 7A, 7B, 7C and 7D are views illustrating a modified example of an insertion instrument.
Figure 7B:
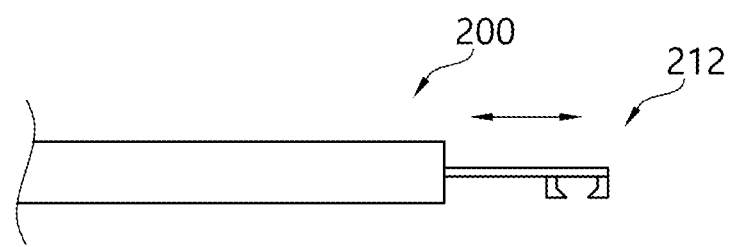
Figure 7C:
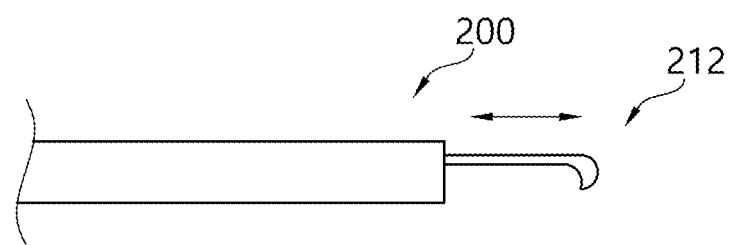
Figure 7D:
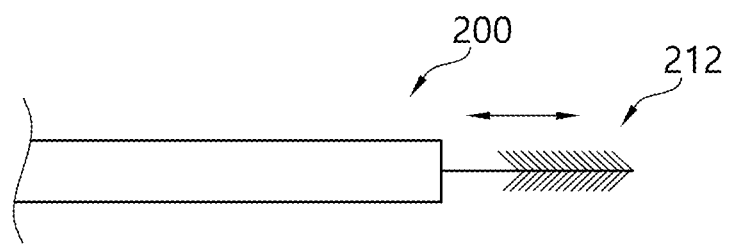

FIGS. 7A, 7B, 7C and 7D are views illustrating a modified example of the insertion instrument 200. As illustrated in FIG. 7a, the insertion instrument 200 may be provided with an extraction part 212 configured to be retractable from an end portion of the tube. The extraction part 212 may be configured as a basket type composed of a plurality of wires. In addition, as illustrated in FIG. 7B, the extraction part may be configured as a clip type configured to grab tissues. In addition, as illustrated in FIG. 7C, the extraction part may be configured as a spoon type capable of scratching tissues. Also, as illustrated in FIG. 7D, the extraction part may be configured as a brush type capable of sweeping away tissues. However, the configuration of the above-described extraction part is merely an example, and may be modified into various configurations capable of capturing cells or extracting tissues.

Figure 8:
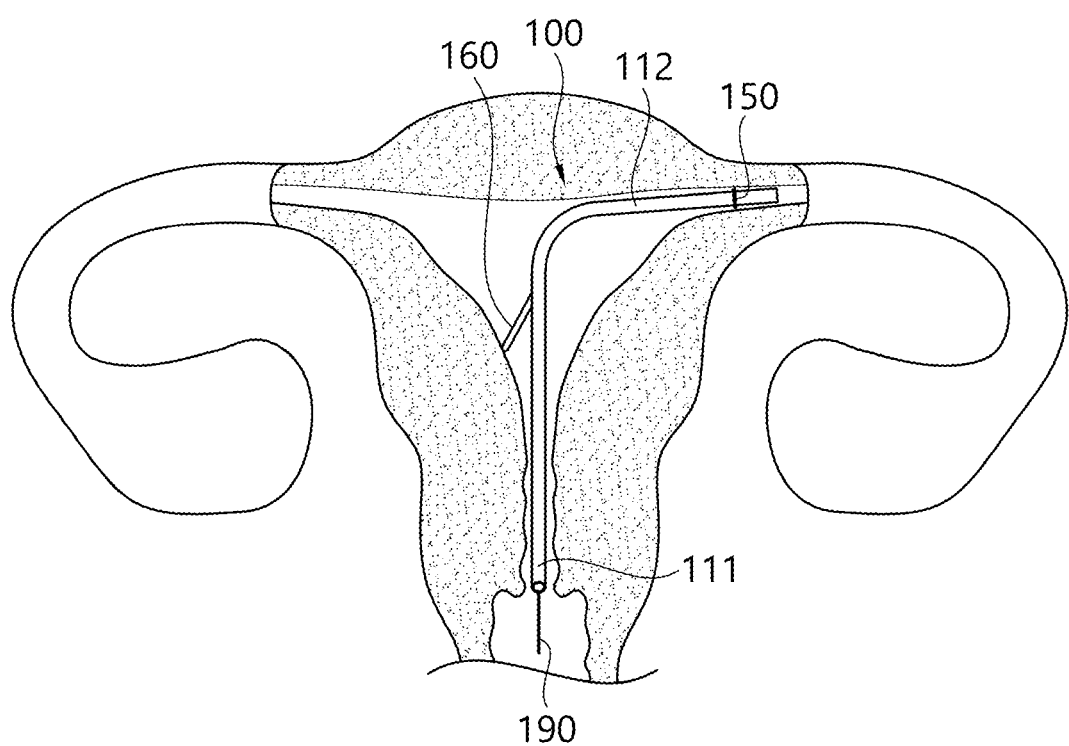
FIG. 8 is a conceptual diagram illustrating a state in which an implant, which is another embodiment, is inserted.

FIG. 8 is a conceptual diagram illustrating a state in which the implant 100, which is another embodiment, is inserted. The illustrated drawing illustrates, for example, a case in which an arm needs to be mounted on only one side of the fallopian tube 14 due to individual differences of a patient. In this embodiment, the implant 100 may be modified and applied in a configuration having one body part and one arm to be inserted into the fallopian tube 14 on one side. Meanwhile, since the implant 100 is installed biased to one side in the uterine cavity 12, the support part 160 may be provided at a rather large angle with the body part so that the implant 100 can be mounted while maintaining the installed position thereof. The support part 160 may prevent the implant 100 from coming off in the downward and lateral directions.

Hereinafter, an insertion process of the implant 100 according to the embodiment shown in FIG. 8 will be described in detail with reference to FIGS. 9 to 12B.

Figure 9:
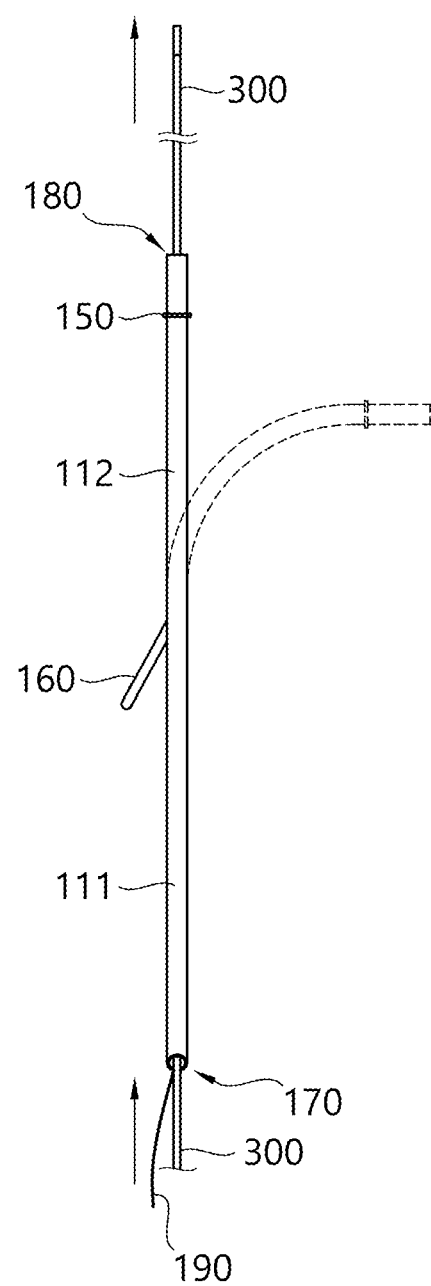
FIG. 9 is a view illustrating an endoscope inserted into the implant.

FIG. 9 is a view illustrating the endoscope 300 inserted into the implant 100, and FIGS. 10 to 12 are conceptual views illustrating the insertion process of the implant 100.

As illustrated in FIG. 9, as a preparation step, the endoscope 300 is inserted into the working channel 130 through the first opening 170, the implant 100 passes through and is withdrawn toward the second opening 180. Here, due to the rigidity of the endoscope 300, the body part and the arm may be deformed into a shape similar to a straight line. A length of the endoscope 300 withdrawn toward the arm may be greater than or equal to a length that can reach the entrance of the fallopian tube 14 from the cervix 13.

Figure 10A:
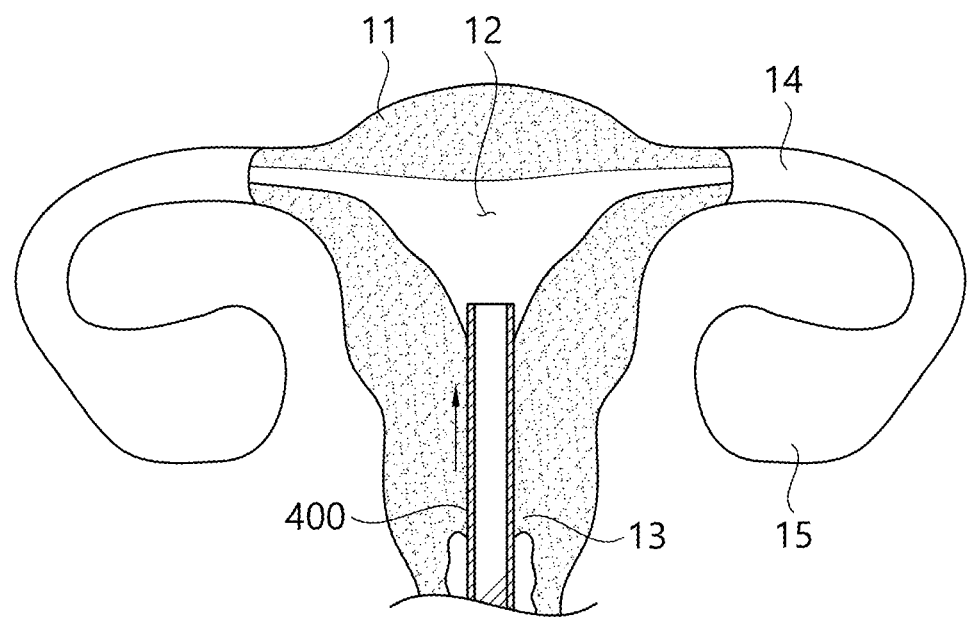
FIGS. 10A, 10B, 11A, 11B, 12A and 12B are conceptual views illustrating an implant insertion process.

Thereafter, as illustrated in FIG. 10A, a sheath 400 is inserted from the cervix 13 to secure a path from the vaginal canal 16 to the uterine cavity 12. Although not illustrated, an operation of changing the shape of the uterus 11 by pulling the cervix 13 so that the sheath 400 can be easily inserted may be performed.

Figure 10B:
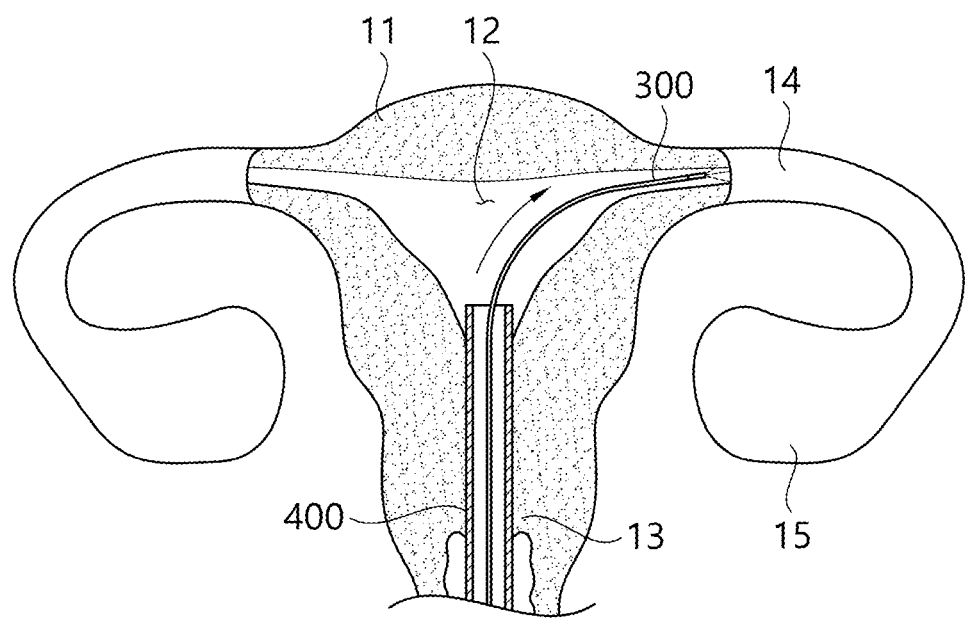

Thereafter, as illustrated in FIG. 10B, the endoscope 300 inserted into the vaginal canal 16 passes through the cervix 13 and the uterine cavity 12 through the channel of the sheath 400 and is then inserted into the fallopian tube 14. In inserting of the endoscope 300, it may be possible to operate and insert the endoscope 300 while checking an image acquired by the endoscope 300.

Figure 11A:
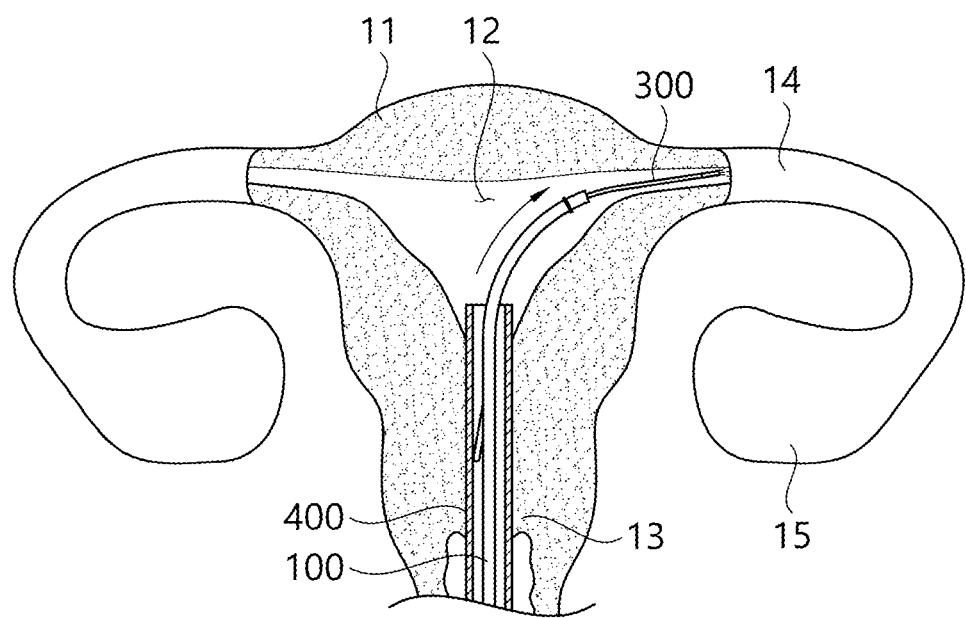

Thereafter, as illustrated in FIG. 11a, the implant 100 is inserted into the uterine cavity 12 through the inside of the vaginal canal 16, that is, the channel of the sheath 400. Here, while the endoscope 300 is fixed, only the implant 100 advances. At this point, although not illustrated, a separate tool is provided for advancing the implant 100 so that it is possible to insert the implant 100 while supporting a fixing part of the implant 100. The implant 100 may be guided by the endoscope 300 because the endoscope 300 is inserted into the working channel 130, and as the endoscope 300 is inserted, the arm, which is the most distal end portion of the implant 100, is inserted toward the fallopian tube 14 along the endoscope 300.

Figure 11B:
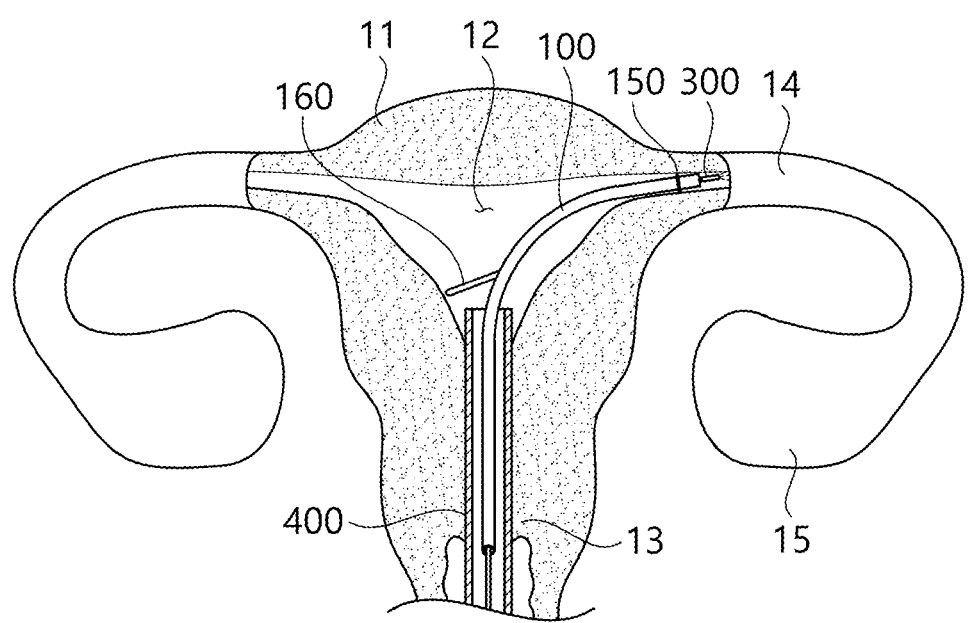

Thereafter, as illustrated in FIG. 11B, an end portion of the arm is inserted into the fallopian tube 14 along the endoscope 300, and the protrusion 150 is inserted into the fallopian tube 14 so that the arm can be mounted. At this point, the support part 160 is separated from the sheath 400 and is unfolded by a restoring force.

Figure 12A:
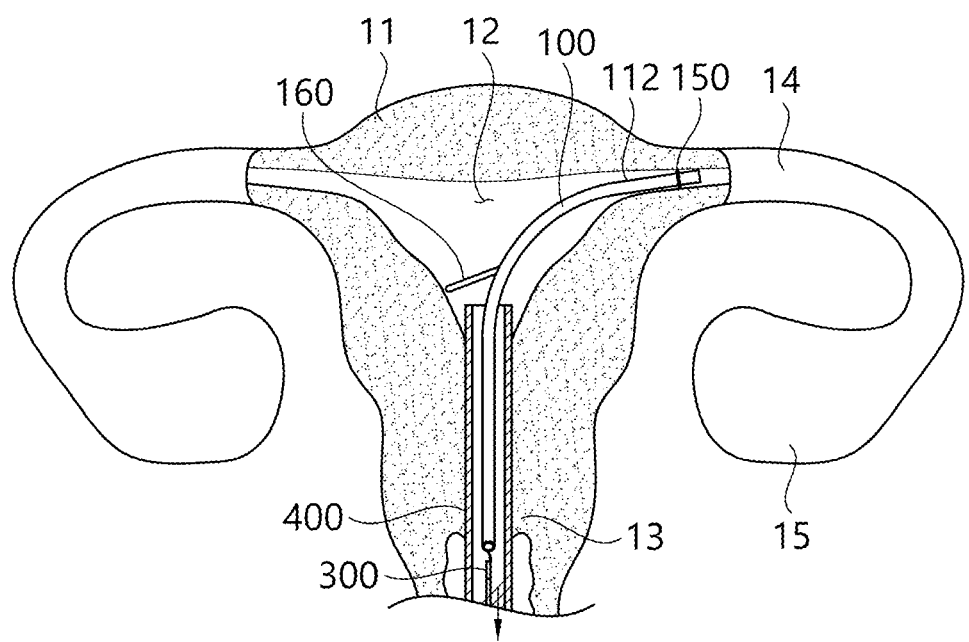
Figure 12B:
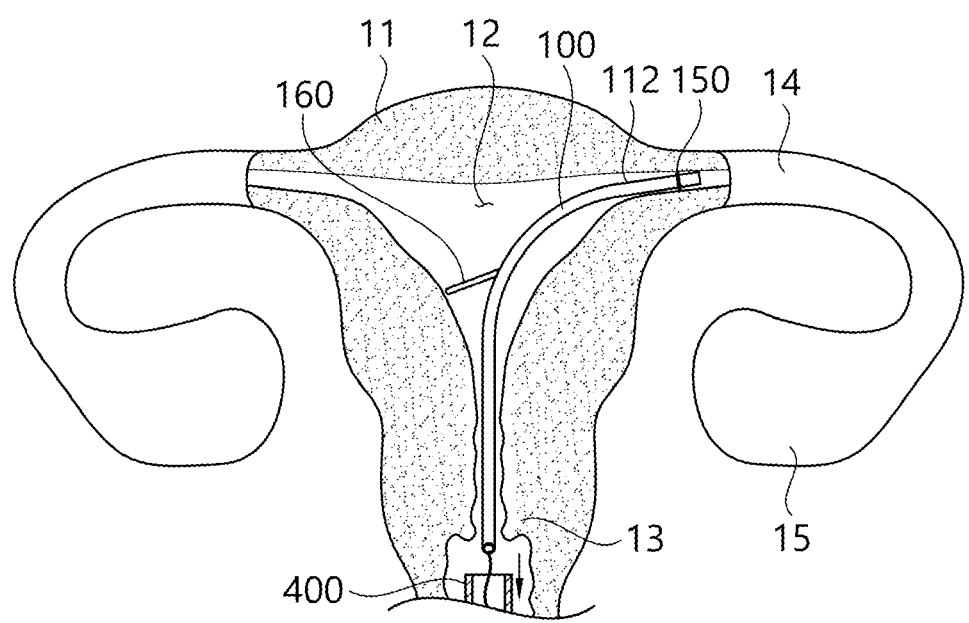

Thereafter, after the endoscope 300 is removed to the outside as shown in FIG. 12A, the sheath 400 is removed as shown in FIG. 12B to complete the installation of the implant 100.

Hereinafter, a screening test using the implant 100 will be described with reference to FIGS. 13A and 13B.

Figure 13A:
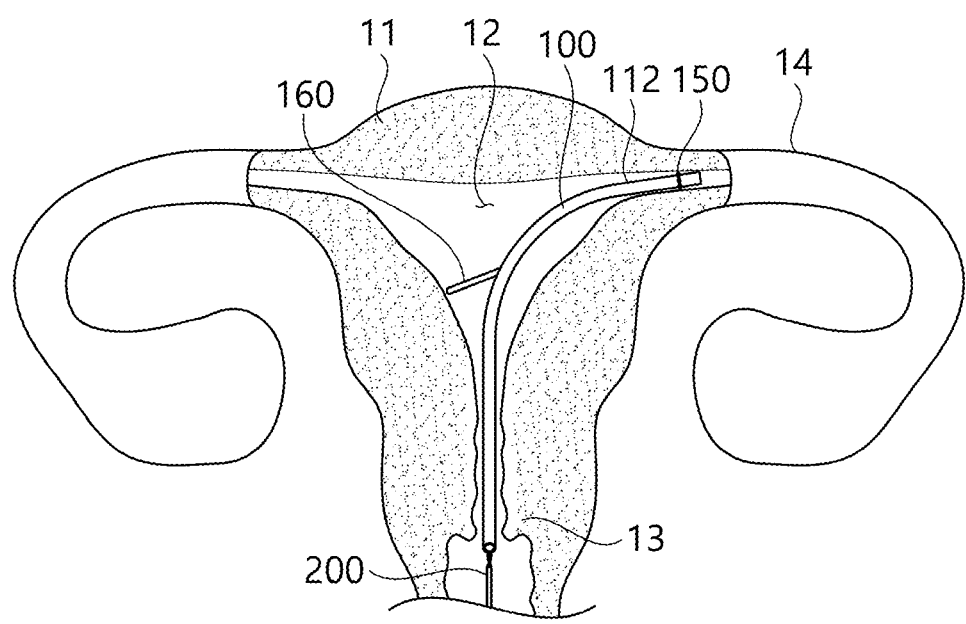
FIGS. 13A and 13B are diagrams of a state of use during cell capture or tissue extraction.
Figure 13B:
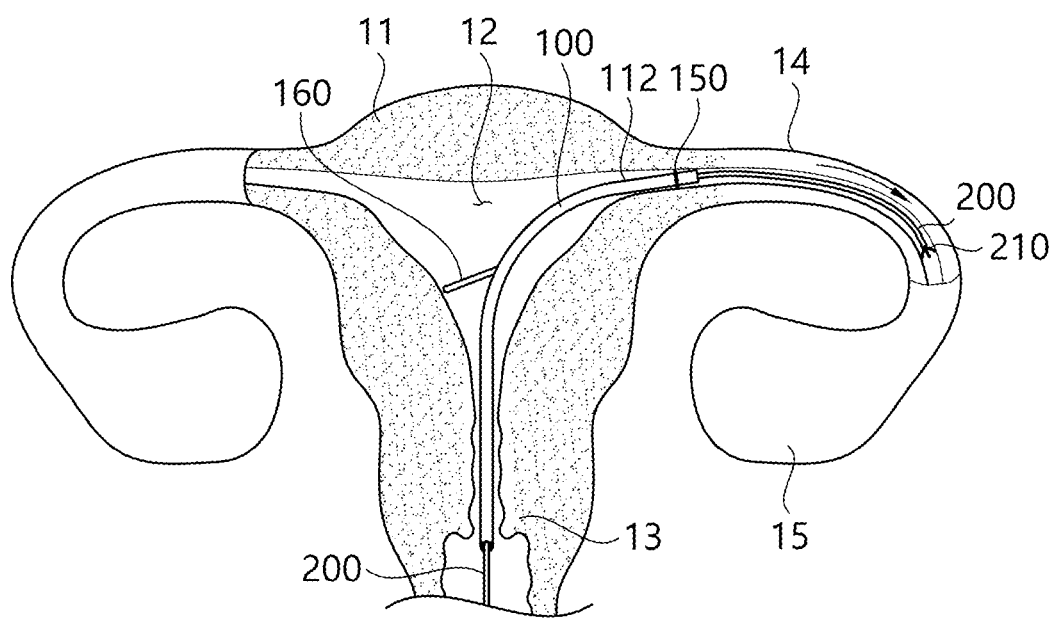

FIGS. 13A and 13B are diagrams of a state of use during cell capture or tissue extraction. As illustrated, the implant 100 may be used when performing a screening test independent of the time of installation. As illustrated in FIG. 13A, when it is necessary to capture cells or extract tissues from the fallopian tube 14 for an ovarian cancer screening test, the insertion instrument 200 is introduced into the vaginal canal 16 and then inserted into the first opening 170 that is exposed from the cervix 13 to the vaginal canal 16. Thereafter, as shown in FIG. 13b, the insertion instrument 200 is inserted along the working channel 130 to the fallopian tube 14. The insertion instrument 200 is inserted by a predetermined length so as to be inserted to a position adjacent to an ovary 15. When the insertion instrument reaches an inspection position, the insertion instrument 200 is manipulated to capture cells or to extract tissues and take out the cells or tissues.

Meanwhile, in relation to the screening test, an insertion length of the insertion instrument 200 may be determined based on a length of the working channel 130 and a length of the fallopian tube 14. That is, the insertion length may determine a length by which an end portion of the insertion instrument 200 reaches the fallopian tube 14 through the working channel 130 to move to a position adjacent to the ovary 15.

Meanwhile, although not illustrated, early diagnosis of the serous tubal intraepithelial carcinomas (STICs) of the fallopian tubes may be performed by performing tests such as genetic tests and malignant cell tests on the captured cells or the extracted tissue from the fallopian tubes 14.

Hereinafter, an ovarian cancer screening test method using an implant, which is another embodiment according to the present disclosure, will be described in detail with reference to FIGS. 14 and 15.

Figure 14:
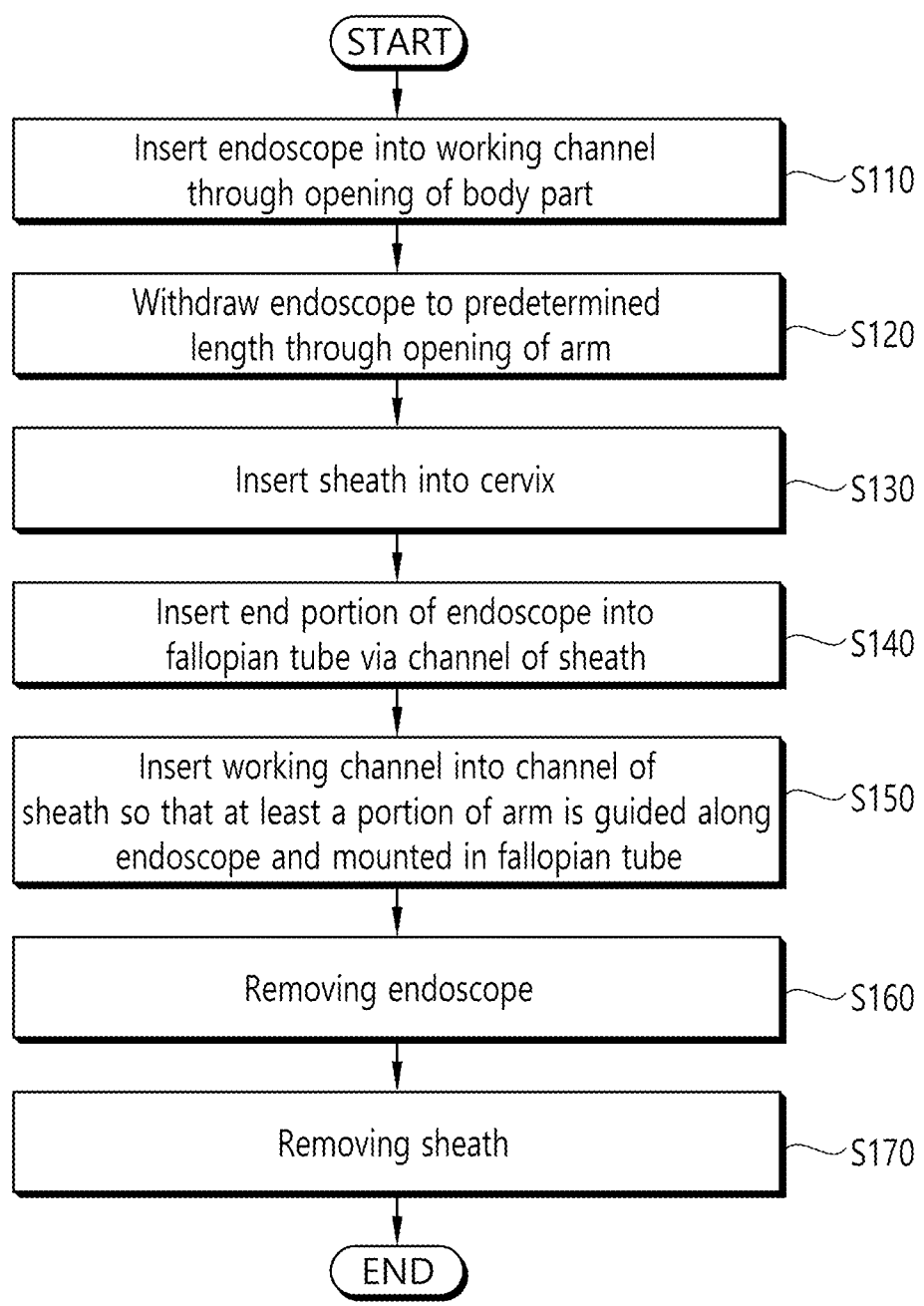
FIG. 14 is a flowchart of an implant insertion process.

FIG. 14 is a flowchart of an implant insertion process. As illustrated, insertion of an implant is performed by inserting an endoscope into a working channel through an opening of a body part in operation S110, withdrawing the endoscope by a predetermined length through the opening of an arm in operation S120, inserting a sheath into cervix in operation S130, inserting an end portion of the endoscope through the channel of the sheath into a fallopian tube in operation S140, inserting the implant into uterine cavity through the channel of the sheath and inserting at least a portion of the arm into the fallopian tube along the endoscope in operation S150, removing the endoscope in operation S160, and removing the sheath in operation S170.

The implant is inserted before a screening test and may be placed in the uterus for the lifetime of the implant. The implant is configured to be used repeatedly during a periodic screening tests during a period while the implant is mounted.

In the insertion of the implant, the operation S110 of inserting the endoscope into the working channel through the opening of the body part and the operation in operation S120 of withdrawing the endoscope by a predetermined length through the opening of the arm correspond to the preparation operations for inserting the implant. Since the endoscope is provided with bulky elements such as a handpiece or a connector at the rear end of the structure, the endoscope cannot pass through the working channel. Therefore, the endoscope may be first inserted into the implant so that the endoscope can be smoothly pulled out after guiding the insertion of the implant.

The operation S130 of inserting the sheath into the cervix is an operation of providing an entry space so that the implant can be smoothly inserted into the uterine cavity. Meanwhile, in this operation, the sheath is given as an example, but a hysteroscope provided with a working channel may be used. In a case where the hysteroscope is used, the hysteroscope may perform an additional screening test by acquiring an image of the uterine cavity while entering the uterine cavity, and the final placement state of the implant may be checked through an image.

The operation S140 of inserting the end portion of the endoscope into the fallopian tube through the sheath channel corresponds to an operation of first entering the endoscope so that a path in which the end portion of the arm of the implant is inserted into the fallopian tube is securing and guided. A user may insert the endoscope into the fallopian tube through isthmus of the fallopian tube while checking an image captured by the endoscope.

The operation S150 of inserting the implant into the uterine cavity through the channel of the sheath channel and inserting at least a portion of the cancer into the fallopian tube along the endoscope corresponds to an operation of fixing the endoscope with the end portion of the endoscope inserted into the fallopian tube and advancing the implant into the uterine cavity. At this point, the implant is pushed into the sheath while the rear end of the implant is supported. The implant is guided along the endoscope in a way such that the end of the arm first enters the sheath and a part of the arm including the protrusion is finally inserted into the fallopian tube and fixed.

The operation S160 of removing the endoscope corresponds to an operation of withdrawing the endoscope out of the human body while the implant is fixed.

The operation S170 of removing the sheath is an operation of removing the sheath inserted into the uterus.

The aforementioned implant enters with the support part in a folded state when passing through the sheath, and is configured to be spread out in the uterine cavity and mounted in the uterus. As soon as the support part comes out of the sheath, the support part is unfolded by its own elasticity. The timing at which the support part comes out of the sheath may occur during the insertion of the implant into the uterine cavity or during the removal of the sheath.

Meanwhile, although not illustrated, the implant may be guided and inserted using a guide wire instead of the endoscope. At this point, it is possible to use a separate imaging device to insert an end portion of the guide wire into a fallopian tube.

Figure 15:
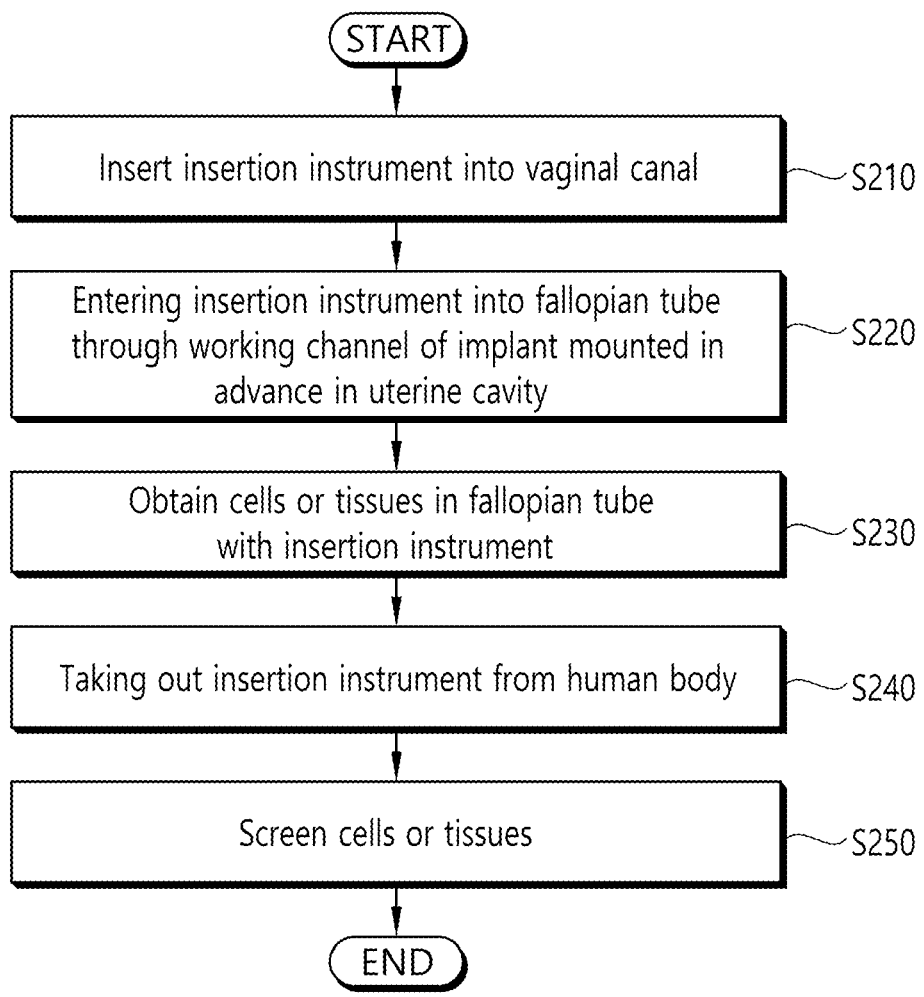
FIG. 15 is a flowchart of a screening test method using an implant, which is another embodiment according to the present disclosure.

FIG. 15 is a flowchart of a screening test method using an implant, which is another embodiment according to the present disclosure.

As illustrated in FIG. 15, a screening test method using an implant includes inserting an insertion instrument into vaginal canal in operation S210, entering the insertion instrument into a fallopian tube through a working channel of an implant mounted in advance in uterine cavity in operation S220, obtaining cells or tissues in the fallopian tube with the insertion instrument in operation S230, withdrawing the insertion instrument out of the human body in operation S240, and screening the cells or tissues in operation S250.

Meanwhile, although not illustrated, in a case where the inserted implant is of a length at which the implant is not exposed to vaginal canal and the implant is mounted in the uterine cavity, an operation of pulling a fiber provided in the implant to expose an opening of the working channel to the vaginal canal may be performed first.

The operation S210 of inserting the insertion instrument into the vaginal canal is an operation of inserting the insertion instrument for capturing cells or extracting tissues from the fallopian tube in a state in which the vaginal canal is expanded.

The operation S220 of entering the insertion instrument into the fallopian tube through the working channel of the implant mounted in advance in the uterine cavity corresponds to an operation of inserting the insertion instrument into the working channel of the implant exposed to the cervix. In a case where the insertion instrument is inserted into the working channel, the insertion instrument may be smoothly inserted along the working channel up to the fallopian tube even without a separate operation. Meanwhile, a sampling position may vary depending on an insertion length. For example, when the insertion length is increased, sampling may be performed at a position adjacent to the ovary, and when the insertion length is shortened, sampling may be performed at a position adjacent to the uterus.

The operation S230 of obtaining cells or tissues in the fallopian tube with the insertion instrument is an operation of performing sampling by operating the insertion instrument in the fallopian tube. The insertion instrument may be configured to contact the inner wall of the fallopian tube to obtain cells or tissues or to extract body fluid within the fallopian tube. However, since various configurations may be applied to the insertion instrument, a detailed description of the configuration will be omitted.

The operation S240 of withdrawing the insertion instrument out of the human body corresponds to an operation of withdrawing the insertion instrument out of the human body while protecting the captured cells or the extracted tissues. The insertion instrument may be operated while moving in the opposite direction to an insertion direction through the working channel.

The operation S250 of screening the cells or tissues corresponds to an operation of screening for ovarian cancer by performing a test on a sample extracted from the fallopian tube. For example, screening for serous tubal intraepithelial carcinomas (STICs) of the fallopian tube may be performed.

The above-described ovarian cancer screening test method using an implant may be performed repeatedly in periodic screening tests performed at predetermined intervals after the first placement of the implant or in a regular screening tests.

As described above, according to the implant for screening test of ovarian cancer, the screening test kit comprising same, and the ovarian cancer screening test method using same of the present disclosure, the implant mounted in the uterus can be used to execute the screening test, can simply carry out periodically repeated screening tests to improve the convenience and minimize discomfort for the patient, and can allow both cystoscopy and biopsy.

The invention claimed is:

1. An implant comprising:
a body part extending to a predetermined length so as to be inserted into a uterine cavity;
an arm extending from the body part and having at least a portion to be inserted into a fallopian tube; and
a working channel formed through the arm from an end portion of the body part, and configured to allow an insertion instrument to be inserted therein from an outside,
wherein the implant is installed in the uterine cavity so that the working channel maintains a path from a cervix to the fallopian tube,
wherein the body part is a first body part, the arm is a first arm, the working channel is a first working channel, the implant further comprising a second body part, a second arm, and a second working channel that have the same configurations as the first body part, the first arm, and the first working channel, respectively, to form a symmetrical pair, and
wherein the implant further comprises a support part including a central portion connected to the first body part and the second body part and extending to front and rear sides of a uterus to support an inner wall of the uterus.

2. The implant of claim 1, wherein the implant is inserted into the uterine cavity through the cervix, and at least a portion of the implant is formed of a soft material so that the implant is installed in the uterus in a state at least a portion of the arm is inserted into the fallopian tube.

3. The implant of claim 2, wherein at least one of the body part and the arm comprises a curved portion.

4. The implant of claim 2, wherein the implant further comprises a protrusion that prevents the arm from coming off from the fallopian tube in a case where the implant is installed in the uterine cavity.

5. The implant of claim 2, wherein the working channel comprises a tapered portion formed at the end portion of the body part so as to smoothly guide the insertion of the insertion instrument.

6. The implant of claim 1, wherein the first working channel extends from a first opening at the end portion of the first body part to a second opening at an end portion of the first arm, and
wherein a door is detachably coupled to the first opening to selectively open and close the first working channel.

* * * * *